(12) United States Patent
Chen et al.

(10) Patent No.: US 11,741,813 B2
(45) Date of Patent: Aug. 29, 2023

(54) FALL DETECTION SYSTEM AND METHOD

(71) Applicant: Climax Technology Co., Ltd., Taipei (TW)

(72) Inventors: Yi-Kai Chen, Taipei (TW); Yu-Hua Hu, New Taipei (TW)

(73) Assignee: Climax Technology Co., Ltd., Taipei (TW)

(*) Notice: Subject to any disclaimer, the term of this patent is extended or adjusted under 35 U.S.C. 154(b) by 281 days.

(21) Appl. No.: 17/339,739

(22) Filed: Jun. 4, 2021

(65) Prior Publication Data

US 2022/0392325 A1 Dec. 8, 2022

(51) Int. Cl.
G08B 21/04 (2006.01)
A61B 5/11 (2006.01)
G01S 7/41 (2006.01)
G01S 13/88 (2006.01)
G01S 13/42 (2006.01)

(52) U.S. Cl.
CPC .......... *G08B 21/043* (2013.01); *A61B 5/1117* (2013.01); *G01S 7/411* (2013.01); *G01S 7/417* (2013.01); *G01S 13/42* (2013.01); *G01S 13/886* (2013.01)

(58) Field of Classification Search
None
See application file for complete search history.

(56) References Cited

U.S. PATENT DOCUMENTS

| | | | |
|---|---|---|---|
| 7,567,200 B1* | 7/2009 | Osterweil | G01S 13/56 342/28 |
| 7,916,066 B1* | 3/2011 | Osterweil | A61B 5/1117 382/115 |
| 11,341,716 B1* | 5/2022 | Chen | G06V 20/20 |
| 2019/0108740 A1 | 4/2019 | Coke et al. | |
| 2020/0143656 A1* | 5/2020 | Li | G08B 21/043 |
| 2020/0166611 A1* | 5/2020 | Lin | G01S 13/0209 |
| 2021/0142643 A1* | 5/2021 | Susna | A61B 5/7264 |
| 2021/0173045 A1* | 6/2021 | Hu | G01S 7/415 |

(Continued)

FOREIGN PATENT DOCUMENTS

CN 111887861 A 11/2020
WO WO-2017118610 A1 * 7/2017 ........... A61B 5/0024

OTHER PUBLICATIONS

Fall Detection Using Deep Learning in Range-Doppler Radas Feb. 2018 (Year: 2018).*

(Continued)

*Primary Examiner* — Fekadeselassie Girma
(74) *Attorney, Agent, or Firm* — Donald E. Stout; Stout, Uxa & Buyan, LLP

(57) ABSTRACT

A fall detection system includes a radar that generates emitting radio waves and receives reflected radio waves from a person under detection, a data generator that generates a point cloud according to the reflected radio waves, an area determining device that determines a sub-area of a detecting area in which the person under detection lies, and a classifier that determines whether the person under detection falls according to the point cloud. The classifier adaptively processes the point cloud with different methods according to sub-areas as determined by the area determining device respectively to determine whether the person under detection falls.

18 Claims, 2 Drawing Sheets

(56) References Cited

U.S. PATENT DOCUMENTS

2022/0392325 A1* 12/2022 Chen ..................... G01S 7/417

OTHER PUBLICATIONS

Nageswaran, Nagesh, "High-Resolution Radar Based Object Classification for Automotive Applications", URL: https://kluedo.ub.uni-kl.de/files/6279/high resolution radar based road user classification.pdf, Dec. 31, 2016.
Extended European Search Report dated Nov. 22, 2021 in related European Application No. 21177938.4.

* cited by examiner

FALL DETECTION SYSTEM AND METHOD

BACKGROUND OF THE INVENTION

1. Field of the Invention

The present invention generally relates to fall detection, and more particularly to an adaptive fall detection system and method.

2. Description of Related Art

Fall of the elderly is a universal and serious health issue. Early discovery and report of the fall may facilitate prompt medical treatment. A wearable detection device, belonging to contact-type detection device, is one of conventional fall detection schemes. The wearable detection device causes inconveniency as a user should wear the device at all times.

Another of conventional fall detection schemes utilizes an image capture device (e.g., camera) to capture images continuously and analyzes image content to determine whether a person under detection falls. This scheme belongs to non-contact (or contactless) type detection device, for example, as disclosed in U.S. patent application Ser. No. 17/085,683 entitled "FALL DETECTION AND REPORTING TECHNOLOGY," contents of which are hereby incorporated by reference. Nevertheless, this scheme cannot retain personal privacy and is thus not adaptable to some occasions such as bathrooms.

A further one of conventional fall detection schemes utilizes a radar device to emit radio waves and analyzes reflected radio waves to determine whether a person under detection falls. This scheme belongs to non-contact type detection device, for example, as disclosed in U.S. patent application Ser. No. 16/590,725 entitled "DETECTION METHOD, DETECTION DEVICE, TERMINAL AND DETECTION SYSTEM," contents of which are hereby incorporated by reference. Nevertheless, the emitting and reflection of the radio waves of the radar device cannot achieve comprehensive coverage such that some partial area may possess low detection accuracy, resulting in false reports that waste manpower and resource or miss reports that cause loss of medical treatment opportunities.

A need has thus arisen to propose a novel detection scheme to overcome drawbacks of the conventional fall detection.

SUMMARY OF THE INVENTION

In view of the foregoing, it is an object of the embodiment of the present invention to provide a fall detection system and method capable of adaptively processing a point cloud with different methods according to sub-areas in which a person under detection lies. Accordingly, the accuracy of fall detection may be greatly improved, and false reports and miss reports may be substantially reduced.

According to one embodiment, a fall detection system includes a radar, a data generator, an area determining device and a classifier. The radar generates emitting radio waves and receives reflected radio waves from a person under detection. The data generator generates a point cloud according to the reflected radio waves. The area determining device determines a sub-area of a detecting area in which the person under detection lies. The classifier determines whether the person under detection falls according to the point cloud. The classifier adaptively processes the point cloud with different methods according to sub-areas as determined by the area determining device respectively to determine whether the person under detection falls.

DETAILED DESCRIPTION OF THE INVENTION

Figure 1:
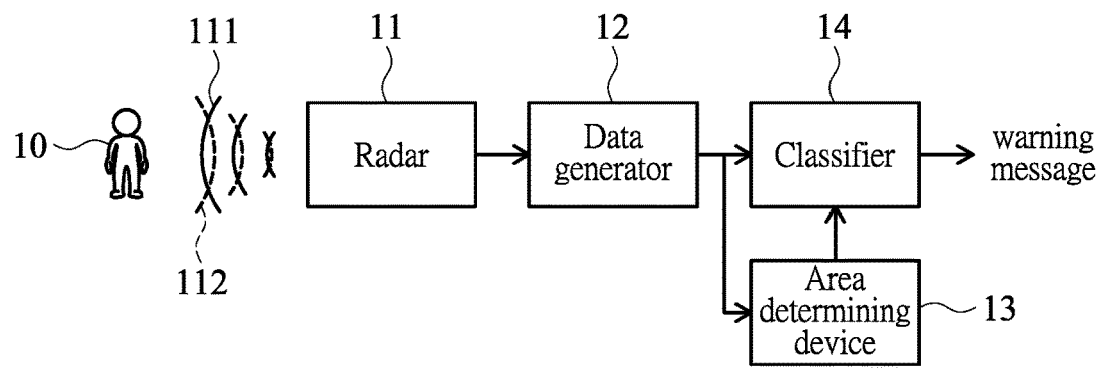
FIG. 1 shows a block diagram illustrating a fall detection system according to one embodiment of the present invention.
Figure 2:
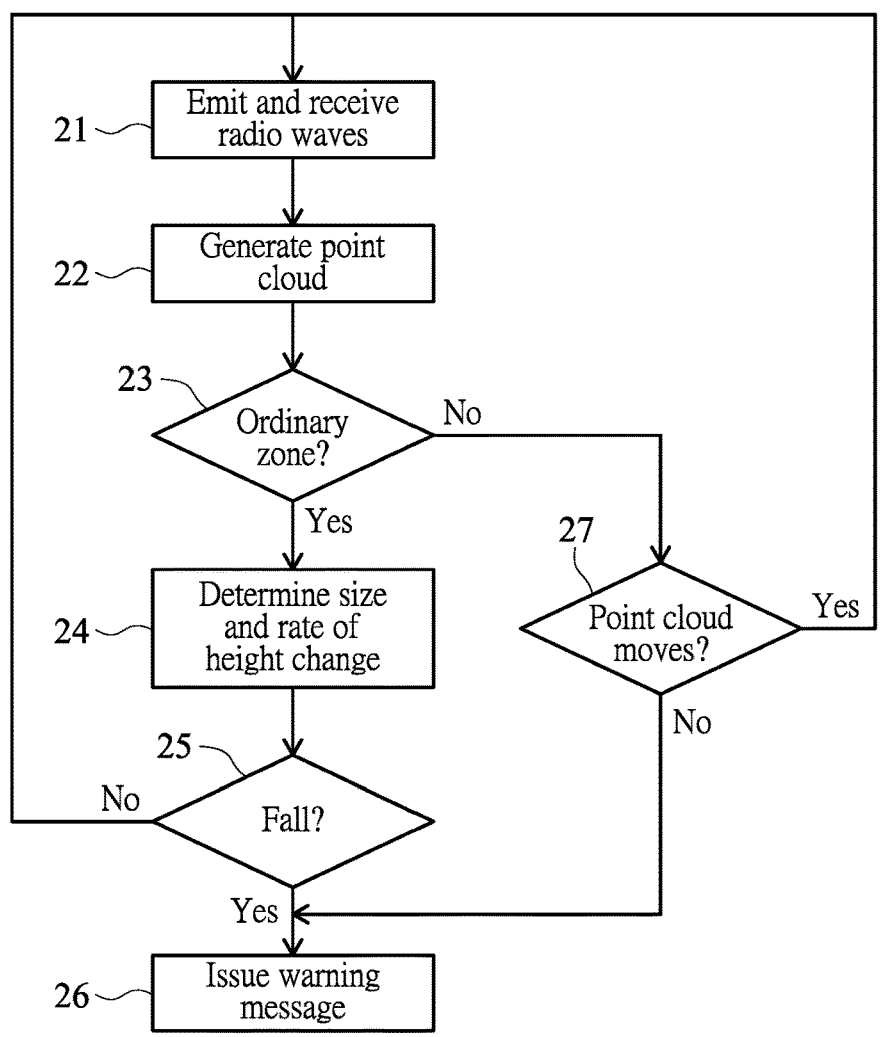
FIG. 2 shows a flow diagram illustrating a fall detection method according to one embodiment of the present invention.

FIG. 1 shows a block diagram illustrating a fall detection system 100 according to one embodiment of the present invention, and FIG. 2 shows a flow diagram illustrating a fall detection method 200 according to one embodiment of the present invention. Although fall detection adapted to elderly care is exemplified in the embodiment, it is appreciated that the invention may be adaptable to other applications such as fall detection for toddlers.

The fall detection system 100 of the embodiment may include a radar 11 configured to generate emitting radio waves 111 and to receive reflected radio waves 112 from a person 10 under detection (step 21). In the embodiment, the radar 11 may include a millimeter wave (mmWave) radar, which has frequency range of about 30 to 300 GHz and wavelength range of about 1 to 10 mm. In one embodiment, the radar 11 may include an ultra-wideband (UWB) radar adaptable to short-range and low-power applications.

The fall detection system 100 of the embodiment may include a data generator 12 configured to generate a point cloud according to the reflected radio waves (step 22). The point cloud includes a plurality of three-dimensional (3D) data representing the 3D shape of the person 10 under detection. Generally speaking, a point cloud refers a set of data points in space representing a 3D shape of an object, and each data point has 3D coordinates.

The fall detection system 100 of the embodiment may include an area determining device 13 configured to determine a sub-area of a detecting area in which the person 10 under detection lies. For example, the position of the person 10 under detection may be determined according to the position in which the point cloud concentrates.

Figure 3:
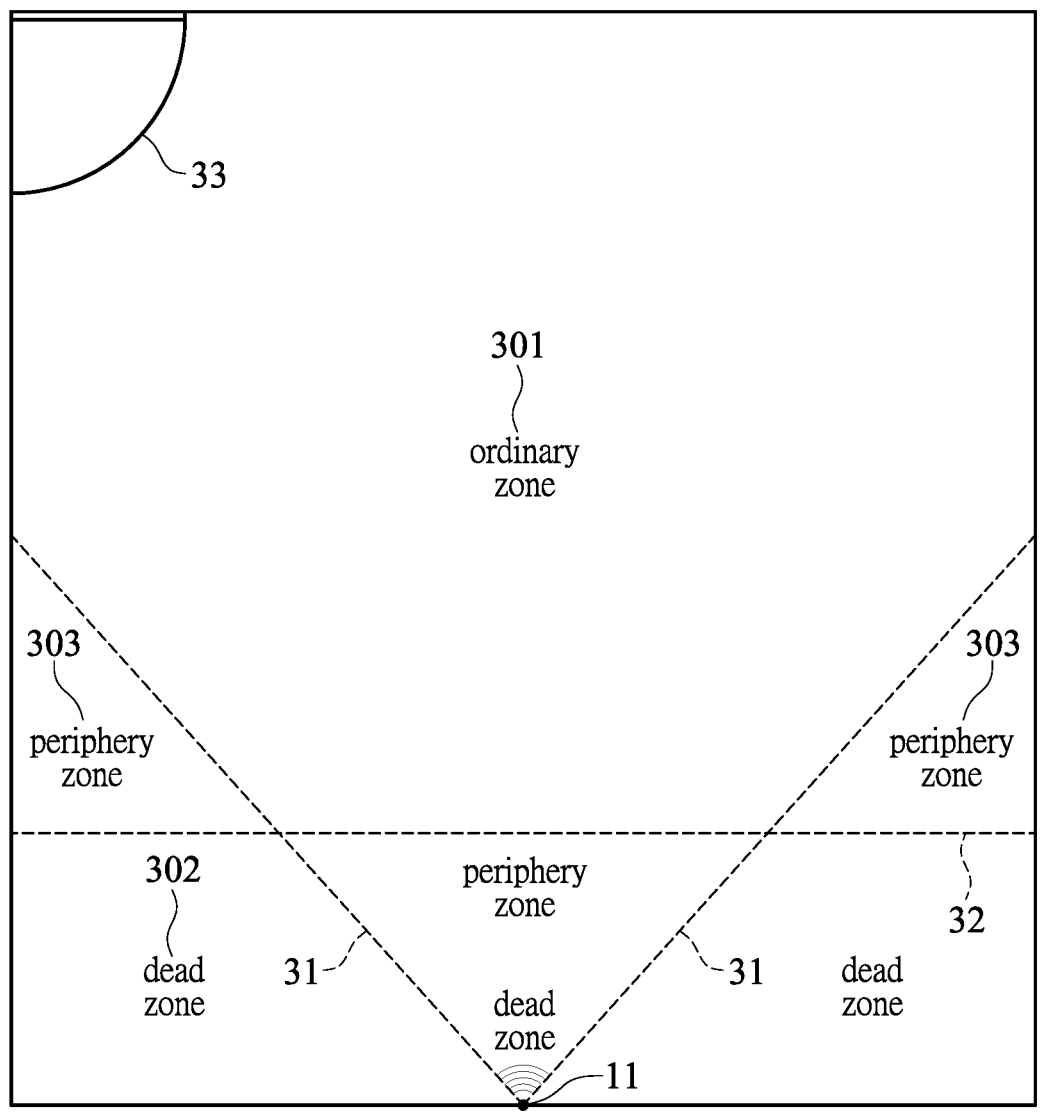
FIG. 3 shows a top view of an exemplary detecting area.

FIG. 3 shows a top view of an exemplary detecting area 300, in which 31 denotes a primary field of view (FOV) line and 32 denotes a peripheral line. The detecting area 300 may be divided into the following sub-areas by the primary FOV line 31 and the peripheral line 32: ordinary zone 301, dead zone 302 and peripheral zone 303. Generally speaking, the ordinary zone 301 refers to an area inside a coverage area of the radar 11 or the FOV line 31, the dead zone 302 refers to an area to which the radar 11 is close and therefore cannot properly receive the reflected radio waves 112, and the peripheral zone 303 refers to an area outside the coverage area of the radar 11 or the FOV line 31. It is noted that radio wave intensity in the ordinary zone 301 is substantially greater than radio wave intensity in the dead zone 302 or the peripheral zone 303, for example, with a ratio thereof being greater than an adjustable threshold. Therefore, accuracy of the point cloud in the ordinary zone 301 is substantially greater than accuracy of the point cloud in the dead zone 302 or the peripheral zone 303.

The detection system 100 of the embodiment may include a classifier 14 configured to determine whether the person 10 under detection falls according to the point could. In one embodiment, the classifier 14 may include a neural network configured to be trained to extract features from the point cloud in order to determine whether the person 10 under detection falls. According to one aspect of the embodiment, the classifier 14 adaptively processes the point cloud with different methods according to sub-areas as determined by the area determining device 13 respectively to determine whether the person 10 under detection falls.

In step 23, the area determining device 13 determines whether the person 10 under detection lies in the ordinary zone 301. If the determination is positive (i.e., the person 10 under detection lies in the ordinary zone 301), the flow goes to step 24.

In step 24, the classifier 14 determines a size and a rate of height change of the point cloud, according to which it determines whether the person 10 under detection falls (step 25). For example, the person 10 under detection is decided to be falling when the size of the point cloud is less than a predetermined first threshold and the rate of height change of the point cloud is greater than a predetermined second threshold. Conventional methods may be adopted when performing steps 24-25, for example, as disclosed in U.S. patent application Ser. No. 16/590,725 entitled "DETECTION METHOD, DETECTION DEVICE, TERMINAL AND DETECTION SYSTEM," contents of which are hereby incorporated by reference.

If the person 10 under detection is decided to be falling in step 25, the flow goes to step 26, in which a warning message is issued; otherwise the flow goes back to step 21.

If the determination in step 23 is negative (i.e., the person 10 under detection lies in the dead zone 302 or the peripheral zone 303), the flow goes to step 27. In step 27, the classifier 14 determines whether the point cloud (representing the person 10 under detection) moves in a predefined period. For example, the point cloud is decided not to move when moving distance of the point cloud in the predetermined period (e.g., 60 seconds) is less than a predetermined threshold. If the point cloud is decided not to move in the predetermined period in step 27, indicating that the person 10 under detection may probably be falling, the flow goes to step 26 to issue a warning message (with a form being the same as or different from the warning message issued when the person 10 under detection falls in the ordinary zone 301); otherwise the flow goes back to step 21. As the fall of the person 10 under detection (in the dead zone 302 or the peripheral zone 303) is determined according to movement of the point cloud in step 27, the radar 11 should be disposed such that a doorway 33 lies in the ordinary zone 301, instead of the dead zone 302 or the peripheral zone 303, in case that the person 10 under detection is erroneously decided to fall just because of leaving the detecting area 300 through the doorway 33.

According to the embodiment as disclosed above, the classifier 14 adaptively process the point cloud with different methods according to sub-areas with different accuracies of the point cloud. Accordingly, the accuracy of fall detection may be greatly improved, and false reports and miss reports may be substantially reduced.

Although specific embodiments have been illustrated and described, it will be appreciated by those skilled in the art that various modifications may be made without departing from the scope of the present invention, which is intended to be limited solely by the appended claims.

What is claimed is:

1. A fall detection system, comprising:
    a radar that generates emitting radio waves and receives reflected radio waves from a person under detection;
    a data generator that generates a point cloud according to the reflected radio waves;
    an area determining device that determines a sub-area of a detecting area in which the person under detection lies; and
    a classifier that determines whether the person under detection falls according to the point cloud;
    wherein the classifier adaptively processes the point cloud representing the person under detection with different methods according to sub-areas where the person under detection lies as determined by the area determining device respectively to determine whether the person under detection falls.

2. The system of claim 1, wherein the radar comprises a millimeter wave radar.

3. The system of claim 1, wherein the detecting area is divided into the following sub-areas:
    an ordinary zone that is an area inside a coverage area of the radar or a field of view line;
    a dead zone that is an area to which the radar is close and therefore cannot properly receive the reflected radio waves; and
    a peripheral zone that is an area outside the coverage area of the radar or the field of view line.

4. The system of claim 3, wherein radio wave intensity in the ordinary zone is substantially greater than radio wave intensity in the dead zone or the peripheral zone.

5. The system of claim 1, wherein the classifier comprises a neural network trained to extract features from the point cloud in order to determine whether the person under detection falls.

6. The system of claim 3, wherein the classifier determines a size and a rate of height change of the point cloud to determine whether the person under detection falls, when the person under detection is determined to lie in the ordinary zone.

7. The system of claim 6, wherein the person under detection is decided to be falling when the size of the point cloud is less than a predetermined first threshold and the rate of height change of the point cloud is greater than a predetermined second threshold.

8. The system of claim 3, wherein the classifier determines whether the point cloud moves in a predefined period, when the person under detection is determined not to lie in the ordinary zone.

9. The system of claim 8, wherein the person under detection is decided to be falling when moving distance of the point cloud in the predetermined period is less than a predetermined threshold.

10. A fall detection method, comprising:
    generating emitting radio waves and receiving reflected radio waves from a person under detection;
    generating a point cloud according to the reflected radio waves;
    determining a sub-area of a detecting area in which the person under detection lies; and
    determining whether the person under detection falls according to the point cloud;
    wherein the point cloud representing the person under detection is adaptively processed with different methods according to sub-areas where the person under detection lies as determined respectively to determine whether the person under detection falls.

11. The method of claim 10, wherein the emitted radio waves are generated by a radar.

12. The method of claim 11, wherein the detecting area is divided into the following sub-areas:
- an ordinary zone that is an area inside a coverage area of the radar or a field of view line;
- a dead zone that is an area to which the radar is close and therefore cannot properly receive the reflected radio waves; and
- a peripheral zone that is an area outside the coverage area of the radar or the field of view line.

13. The method of claim 12, wherein radio wave intensity in the ordinary zone is substantially greater than radio wave intensity in the dead zone or the peripheral zone.

14. The method of claim 10, wherein the point cloud is processed by a neural network trained to extract features from the point cloud in order to determine whether the person under detection falls.

15. The method of claim 12, wherein a size and a rate of height change of the point cloud is determined to decide whether the person under detection falls, when the person under detection is determined to lie in the ordinary zone.

16. The method of claim 15, wherein the person under detection is decided to be falling when the size of the point cloud is less than a predetermined first threshold and the rate of height change of the point cloud is greater than a predetermined second threshold.

17. The method of claim 12, wherein the point cloud is determined whether moves in a predefined period, when the person under detection is determined not to lie in the ordinary zone.

18. The method of claim 17, wherein the person under detection is decided to be falling when moving distance of the point cloud in the predetermined period is less than a predetermined threshold.

* * * * *